United States Patent
Meixner et al.

[11] Patent Number: 6,101,865
[45] Date of Patent: Aug. 15, 2000

[54] GAS SENSOR

[75] Inventors: Hans Meixner, Haar; Susanne Kornely, München; Dieter Hahn, Schwandorf; Hermann Leiderer, Wörth/Donau; Bertrand Lemire; Birgitta Hacker, both of Schierling, all of Germany

[73] Assignee: Siemens Aktiengesellschaft, Munich, Germany

[21] Appl. No.: 09/101,057

[22] Filed: Jun. 29, 1998

[30] Foreign Application Priority Data

Dec. 29, 1995 [DE] Germany .......................... 195 49 147

[51] Int. Cl.$^7$ .......................... G01N 27/16; G01N 27/00; G01N 27/12; H01L 07/00; B32B 09/00
[52] U.S. Cl. .......................... 73/23.32; 73/31.06; 73/31.05; 338/34; 422/98
[58] Field of Search .......................... 73/23.2, 28.04, 73/31.05, 31.06, 61.43, 64.56, 61.44, 23.32; 422/88, 98, 94; 338/34

[56] References Cited

U.S. PATENT DOCUMENTS

| | | | |
|---|---|---|---|
| 3,242,717 | 3/1966 | Matle et al. .......................... | 73/27 |
| 3,966,439 | 6/1976 | Vennos et al. .......................... | 55/270 |
| 4,066,413 | 1/1978 | Segawa et al. .......................... | 23/254 E |
| 4,347,732 | 9/1982 | Leary .......................... | 73/23 |
| 4,358,951 | 11/1982 | Chang .......................... | 73/23 |
| 4,443,781 | 4/1984 | Ohta et al. .......................... | 338/34 |
| 4,447,397 | 5/1984 | Anauchi et al. .......................... | 422/94 |
| 4,453,126 | 6/1984 | Volgyesi .......................... | 324/61 R |
| 4,592,967 | 6/1986 | Komatsu et al. .......................... | 428/697 |
| 4,638,286 | 1/1987 | Nichols .......................... | 338/34 |
| 4,958,514 | 9/1990 | Tatrami et al. .......................... | 73/25.03 |
| 4,977,658 | 12/1990 | Awano et al. .......................... | 29/25.01 |
| 5,296,196 | 3/1994 | Takeshima .......................... | 422/98 |
| 5,367,283 | 11/1994 | Lauf et al. .......................... | 338/34 |
| 5,605,612 | 2/1997 | Park et al. .......................... | 204/429 |
| 5,614,658 | 3/1997 | Moss .......................... | 73/23.31 |
| 5,629,474 | 5/1997 | Williams .......................... | 73/23.2 |
| 5,635,628 | 6/1997 | Fleisher et al. .......................... | 73/31.06 |
| 5,814,719 | 9/1998 | Suzuki et al. .......................... | 73/23.31 |
| 5,958,787 | 9/1999 | Schönfeld et al. .......................... | 436/116 |
| 5,969,232 | 10/1999 | Schonauer et al. .......................... | 73/31.05 |

Primary Examiner—Hezron Williams
Assistant Examiner—J. David Wiggins
Attorney, Agent, or Firm—Hill Simpson

[57] ABSTRACT

A porous $Al_2O_3$ thick film covers the $SrTiO_3$ layer of an oxygen sensor, said $SrTiO_3$ layer being contacted by means of two Pt electrodes and deposited on an $Al_2O_3$ substrate. The electrically insulating $Al_2O_3$ layer bears a protective layer, which is exposed to the exhaust gas and is preferably also made of $SrTiO_3$. This construction ensures that the output signal of the sensor representing the oxygen partial pressure then depends only on the resistance or, respectively, conductivity value of the non-contaminated $SrTiO_2$ sensor layer.

18 Claims, 3 Drawing Sheets

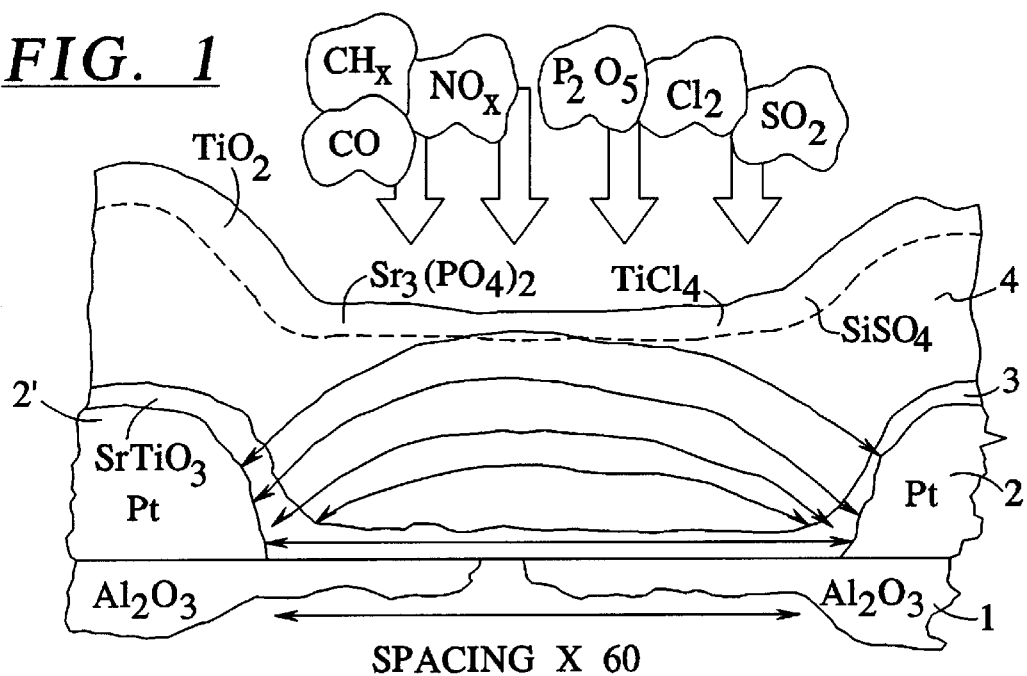
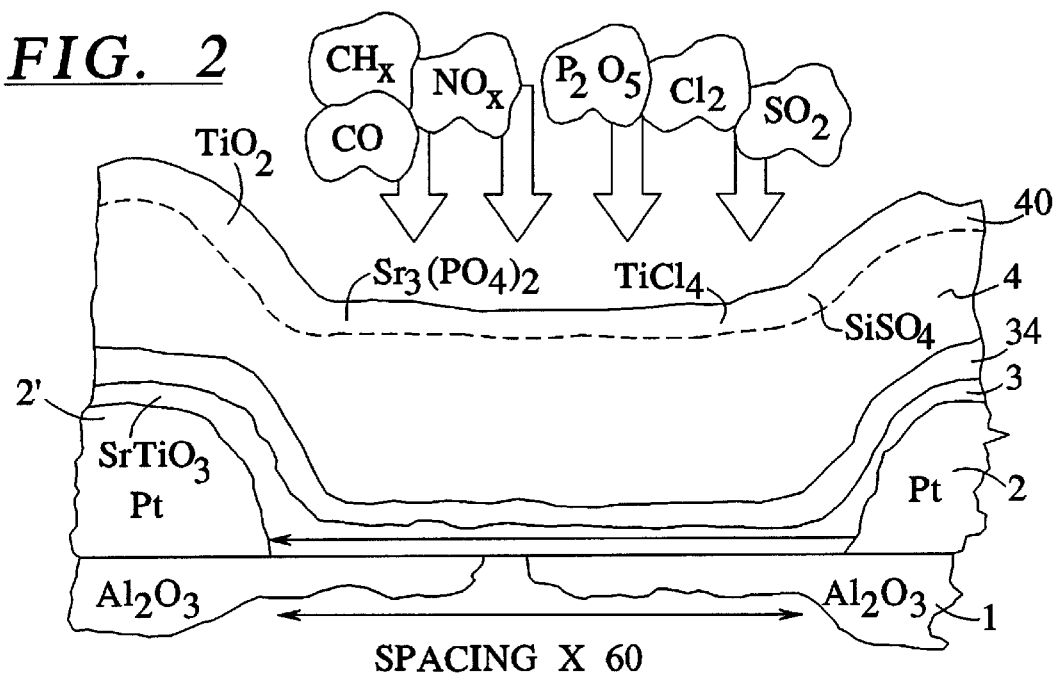

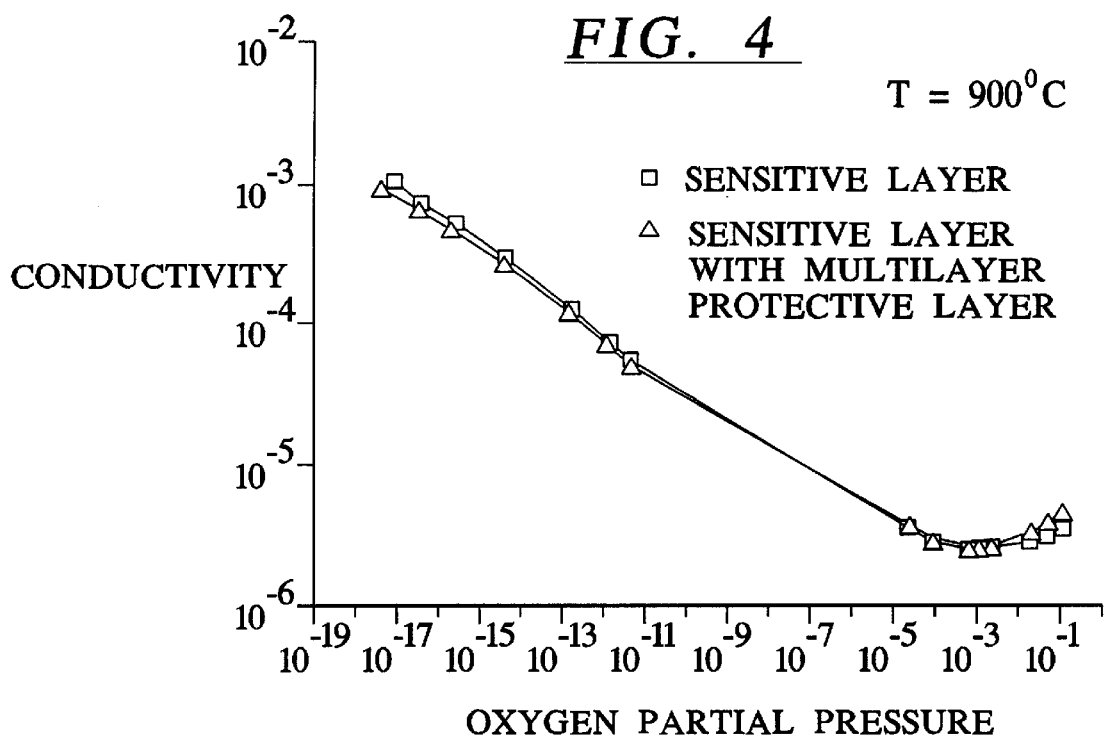
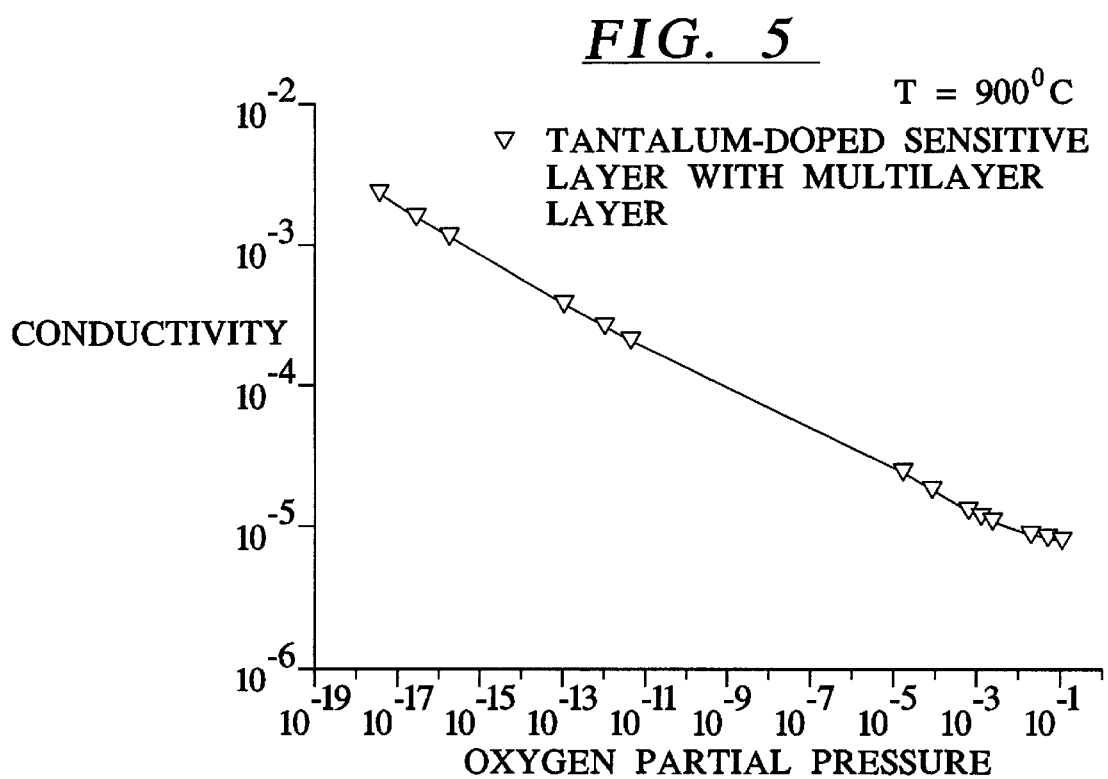

GAS SENSOR

BACKGROUND OF THE INVENTION

1. Field of the Invention

The present invention is directed generally to gas sensors and, more specifically, to gas sensors having a sensor element whose electrical resistance or conductivity depends upon the partial pressure of the gas being detected.

2. Introduction

Exhaust gas sensors are generally exposed to a gas mixture containing several reactive constituents. If the gas-sensitive element consists of a metal oxide, the reversible reciprocal effects that standardly occur at high temperatures (volume reactions, adsorption and desorption processes) of the sensor material with the target gas are exploited in order to measure the concentration or, respectively, partial pressure of this gas. However, the metal oxide often also continues to interact with other constituents of the gas mixture. These can in particular be chemical reactions that can finally lead to the destruction of the sensor layer, which is only a few $\mu$m thick, or, respectively, can irreversibly alter its characteristics. In order to ensure the required long service life and high reliability of the gas sensors, it is absolutely necessary to avoid such reactions. This problem can for example be solved by covering the gas-sensitive sensor regions with a porous protective layer whose material bonds chemically with the materials that damage the metal oxide.

The oxygen sensor of a rapid $\lambda$ probe, known from DE 4339737 C1 and shown in cross-section in FIG. 1, consists essentially of the two comb electrodes 2/2', arranged on an $Al_2O_3$ substrate 1, the oxygen-sensitive $SrTiO_3$ layer 3, and a porous $SrTiO_3$ protective layer 4. The protective layer 4, which completely covers the oxygen-sensitive sensor regions, is exposed to the exhaust gas of an internal combustion engine. Besides nitrogen oxides ($NO_x$), carbon monoxide (CO) and hydrocarbons ($CH_x$), the exhaust gas of a typical internal combustion engine also contains, among others, $SiO_2$, $MnO_2$, $Fe_2O_3$, $P_2O_5$, $Cl_2$, and $SO_2$, due to abrasion and the additives added to the fuel or, respectively, motor oil. The gaseous compounds react with the strontium (Sr) and the titanium (Ti) of the protective layer 4, e.g. to form $TiO_2$, $Sr_3(PO_6)_2$, $TiCl_4$, and thus do not reach the sensitive layer 3. Moreover, the protective layer 4 catches the particles of $SiO_2$, $MnO_2$ and $Fe_2O_3$. The $SrTiO_3$ protective layer 4 considerably prolongs the service life of the known oxygen sensor. However, the observed drift of the sensor signal due to the alteration of the protective layer is disadvantageous.

SUMMARY OF THE INVENTION

An object of the invention is to provide a sensor that can be exposed for longer periods of time to a gas mixture containing aggressive constituents without sustaining damage, and whose output signal also shows only a negligibly small drift even in long-term operation.

In an embodiment, the present invention provides a sensor for detecting at least one gas of a mixture. The gas to be detected has a partial pressure. The gas mixture further includes at least one constituent that is capable of damaging the sensor. The sensor of the present invention comprises a sensor element having an electrical resistance value or conductivity value dependent upon the partial pressure of the gas to be detected. The sensor element is disposed on top of a substrate and is further connected to an electrode system. The sensor element is disposed between the substrate and a porous electrically insulating layer. The porous electrically insulating layer is disposed between the sensor element and a porous top layer. The porous top layer includes a material that bonds chemically with the constituent of the gas that is capable of damaging the sensor element.

In an embodiment, the sensor element further comprises at least one gas-sensitive region and the porous electrically insulating layer covers said gas-sensitive region of the sensor element.

In an embodiment, the porous electrically insulating layer comprises a catalyst.

In an embodiment, the porous top layer comprises a catalyst.

In an embodiment, the porous electrically insulating layer comprises a material selected from the group consisting of $Al_2O_3$, MgO and $SiO_2$.

In an embodiment, the sensor element and the porous top layer are fabricated from the same material.

In an embodiment, the sensor element comprises a semiconducting metal oxide.

In an embodiment, the sensor element comprises a metal oxide doped with a doner.

In an embodiment, the sensor element comprises a material selected from the group consisting of $SrTiO_3$, $BaTiO_3$, $CaTiO_3$, $CeO_2$, $TiO_2$, $Ga_2O_3$, $WO_3$, $AVO_4$ and $FeVO_4$.

In an embodiment, the porous electrically insulating layer completely covers the sensor element.

Other objects and advantages of the present invention will become apparent from reading the following detailed description and appended claims, and upon reference to the accompanying drawings.

BRIEF DESCRIPTION OF THE DRAWINGS

The invention is explained in the following on the basis of the following drawings wherein:

FIG. 1 is a schematic cross-sectional view of an oxygen sensor known in the art;

FIG. 2 is a schematic cross-sectional view of an oxygen sensor made in accordance with the present invention;

FIG. 4 illustrates, graphically, the characteristics of an oxygen sensor known in the art and of an oxygen sensor made in accordance with the present invention; and FIG. 5 illustrates, graphically, the characteristics of an oxygen sensor made in accordance with the present invention, and specifically with a sensor element that has been doped with tantalum.

Figure 3:
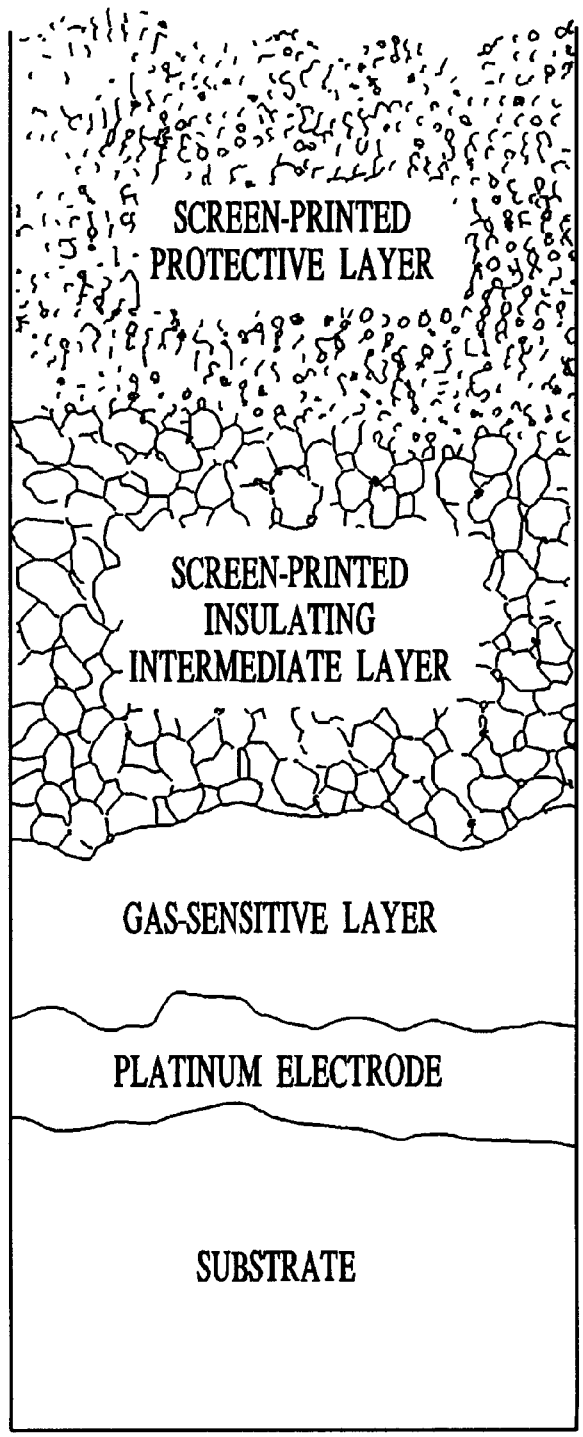
FIG. 3 is a schematic illustration of the layered structure of the oxygen sensor illustrated in FIG. 2.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

Like the oxygen sensor known from DE 4339737 C1, the sensor shown in cross-section in FIGS. 2 and 3 also contains two comb electrodes 2, 2', which are arranged on a substrate 1 of $Al_2O_3$ of BeO, and are made for example of platinum. A layer 3 made of strontium titanate ($SrTiO_3$), which conductively connects the comb electrodes 2/2', serves as an oxygen-sensitive element. The layer 3, which is approximately 1 $\mu$m–50 $\mu$m thick, can be produced by sputtering, screen printing or the use of a CVD method. An electrically insulating porous layer 34 is deposited on it. The layer 34, which is preferably made of aluminum oxide ($Al_2O_3$), magnesium oxide (MgO), or porous silicon oxide ($SiO_2$), and is approximately 3 $\mu$m–100 $\mu$m thick, is produced by means of screen printing or by the use of another thick-film technology method. This layer bears the screen-printed protective layer 4, which is approximately 5 $\mu$m–100 $\mu$m thick and is exposed to the exhaust gas. In the simplest case, the porous protective layer 4 and the oxygen-sensitive layer 3 are produced from the same material. The protective layer 4 thus consists in particular of strontium titanate ($SrTiO_3$), whereby if warranted the $SrTiO_3$ can also contain additives such as, e.g., Ca or Mg. However, temperature-resistance materials that adhere to the insulating layer 34 are also possible, whose chemical behavior is similar to the oxygen-sensitive titanium as regards the reaction with the harmful materials present in the exhaust gas. These materials include e.g. barium titanate ($BaTiO_3$) and calcium titanate ($CaTiO_3$).

For reasons of clarity, the terminal lines allocated to the comb electrodes 2/2', the passivation thereof, the temperature sensor, and Pt resistor layers serving as heating elements, and the housing that contains the sensor are not shown. A description of these constituents can be found in DE 4339737 C1 (see in particular FIGS. 2 to 4 and the associated specification in col. 2, line 30 ff.).

The contaminated region of the protective layer 4 is designated 40 in FIG. 2. Here the products $TiO_2$, $TiCl_4$, $Sr_3(PO_4)_2$, and $SrSO_4$, which result from the reaction of the titanium and strontium with the exhaust gas constituents $P_2O_5$, $Cl_2$, and $SO_2$, are deposited, whereby the composition and thickness of the contaminated layer 40 also changes constantly as a consequence of the contamination by particles of $Fe_2O_3$, $SiO_2$ and $MnO_2$. In the known sensor, this effect leads to a drift of its output signal, since the measured sensor resistance $R_{total}$ or, respectively, the conductivity value $1/R_{total}$ according to equation (1) (series resistors are not taken into account) also depends on the resistance or, respectively, conductivity value of the contaminated layer 40.

$$1/R_{total} = 1/R_{protective\ layer} + 1/R_{contam.\ layer} + 1/R_{sensor\ layer} \quad (1)$$

In contrast, the contamination and the degradation of the protective layer 4 does not influence the output signal of the inventive sensor. Here the $Al_2O_3$ layer 34 provides an electrically insulation of the layer 3, contacted by the comb electrode 2/2', so that the measured conductivity value $1/R_{total}$ is then only a function $f(p_{O2})$ of the oxygen partial pressure $p_{O2}$ (see equation (2)).

FIG. 4 shows the characteristics of an $SrTiO_3$ sensor without a protective layer and of the inventive oxygen sensor. The conductivity of the sensors is shown dependent on the oxygen partial pressure, whereby the sensor temperature was respectively T=900° C. Squares symbolize the measurement values of the $SrTiO_3$ layer, and triangles symbolize the measurement values of the sensor according to FIG. 2. It can be seen that the structure consisting of the insulating layer 34 and the protective layer 4 does not modify the sensor characteristic.

In order to obtain a unambiguous dependence of the conductivity on the partial pressure even given high concentrations of oxygen, the $SrTiO_3$ layer 3 is doped with a donor (Ta, La, W, Nb). As a consequence of this doping, the $O_2$-sensitive material always remains n-conductive within the measurement region of interest, and the conductivity increases constantly as the oxygen partial pressure increases. In FIG. 5, the corresponding characteristic of a Ta-doped $SrTiO_3$ layer (sensor temperature: T=900° C.) is shown. The Ta concentration is approximately 0.1%–1%. In contrast, a occurring $O_2$ partial pressures requires no doping.

If it is desired to use the above-described oxygen sensor as a rapid λ probe, its signal level swing (output signal in lean exhaust gas mixtures / output signal in rich exhaust gas mixtures) should be as large as possible. This can be achieved by providing the insulating intermediate layer 34 and/or the protective layer 4 with a catalyst (Pt, Rh, or mixtures of these materials). The catalyst can be applied e.g. wet-chemically (impregnation with $H_2PtCl_6$ / tempering), sputtering or vapor deposition). It effects a reacting out of the gas mixture to be measured, before it reaches the sensor layer 3. Since the sensor then has to detect very high oxygen partial pressures, it is advantageous to use Ta-doped $SrTiO_3$ as a sensor material. However, metal oxides that are n-conductive in the relevant $O_2$ partial pressure region, such as $CeO_2$, are also possibilities.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

What is claimed is:

1. A sensor for detecting at least one gas of a gas mixture, the gas to be detected having a partial pressure, the gas mixture including at least one constituent capable of damaging the sensor, the sensor comprising:
a sensor element having an electrical resistance value or conductivity value dependent upon the partial pressure of the gas to be detected, the sensor element being disposed on top of a substrate, the sensor element further being connected to an electrode system, the sensor element being disposed between a porous electrically insulating layer and the substrate, the porous electrically insulating layer being disposed between the sensor element and a porous top layer comprising a material that bonds chemically with the constituent of the gas mixture that is capable of damaging the sensor element.

2. The sensor of claim 1 wherein the sensor element further comprises at least one gas-sensitive region, the porous electrically insulating layer covering at least the gas-sensitive region of the sensor element.

3. The gas sensor of claim 1 wherein the porous electrically insulating layer comprises a catalyst.

4. The gas sensor of claim 1 wherein the porous top layer comprises a catalyst.

5. The gas sensor of claim 1 wherein the porous electrically insulating layer comprises a material selected from the group consisting of $Al_2O_3$, MgO and $SiO_2$.

6. The gas sensor of claim 1 wherein the sensor element and the porous top layer are fabricated from a same material.

7. The gas sensor of claim 1 wherein the sensor element comprises a semiconducting metal oxide.

8. The gas sensor of claim 1 wherein the sensor element comprises a metal oxide doped with a donor.

9. The gas sensor of claim 1 wherein the sensor element comprises a material selected from the group consisting of $SrTiO_3$, $BaTiO_3$, $CaTiO_3$, $CeO_2$, $TiO_2$, $Ga_2O_3$, $WO_3$, $A/VO_4$ and $FeVO_4$.

10. The gas sensor of claim 1 wherein the porous electrically insulating layer completely covers the sensor element.

11. A sensor for detecting at least one gas of a gas mixture, the gas to be detected having a partial pressure, the gas mixture including at least one constituent capable of damaging the sensor, the sensor comprising:

a sensor element having an electrical resistance value or conductivity value dependent upon the partial pressure of the gas to be detected, the sensor element comprising at least one gas-sensitive region and a metal oxide doped with a donor, the sensor element being disposed on top of a substrate, the sensor element further being connected to an electrode system, the sensor element being disposed between a porous electrically insulating layer and the substrate, the porous electrically insulating layer comprising a material selected from the group consisting of $Al_2O_3$, MgO and $SiO_2$, the porous electrical insulating layer covering at least the gas-sensitive region of the sensor element, the porous electrically insulating layer being disposed between the sensor element and a porous top layer comprising a material that bonds chemically with a constituent of the gas mixture that is capable of damaging the sensor element.

12. The gas sensor of claim 11 wherein the porous electrically insulating layer comprises a catalyst.

13. The gas sensor of claim 11 wherein the porous top layer comprises a catalyst.

14. The gas sensor of claim 11 wherein the sensor element and the porous top layer are fabricated from a same material.

15. The gas sensor of claim 11 wherein the sensor element comprises a semiconducting metal oxide.

16. The gas sensor of claim 11 wherein the sensor element comprises a material selected from the group consisting of $SrTiO_3$, $BaTiO_3$, $CaTiO_3$, $CeO_2$, $TiO_2$, $Ga_2O_3$, $WO_3$, $A/VO_4$ and $FeVO_4$.

17. The gas sensor of claim 11 wherein the porous electrically insulating layer completely covers the sensor element.

18. A method of measuring an oxygen partial pressure in an exhaust gas of an internal combustion engine, the method comprising the following steps:

providing a sensor element having an electrical resistance value or conductivity value dependent upon the partial pressure of the gas to be detected, the sensor element being disposed on top of a substrate, the sensor element further being connected to an electrode system, the sensor element being disposed between a porous electrically insulating layer and the substrate, the porous electrically insulating layer being disposed between the sensor element and a porous top layer comprising a material that bonds chemically with the constituent of the gas mixture that is capable of damaging the sensor element, exposing the sensor to the exhaust gas stream of the engine, measuring the resistivity or conductivity of the sensor element, calculating the oxygen partial pressure in the exhaust gas based upon the resistivity or conductivity of the sensor element.

* * * * *